(12) United States Patent
Katoozi et al.

(10) Patent No.: US 8,676,335 B2
(45) Date of Patent: Mar. 18, 2014

(54) ON-DEMAND RETRANSMISSION OF DATA WITH AN IMPLANTABLE MEDICAL DEVICE

(75) Inventors: Mehdi Katoozi, Issaquah, WA (US); Kenneth F. Cowan, Kirkland, WA (US); Thomas M. Bocek, Seattle, WA (US); Mark Rutzer, Seattle, WA (US); Scott Vanderlinde, Plymouth, MN (US); Prashant Rawat, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1062 days.

(21) Appl. No.: 12/258,061

(22) Filed: Oct. 24, 2008

(65) Prior Publication Data

US 2009/0048646 A1   Feb. 19, 2009

Related U.S. Application Data

(63) Continuation of application No. 10/870,328, filed on Jun. 17, 2004, now Pat. No. 7,457,669.

(51) Int. Cl.
*A61N 1/00* (2006.01)
*G06F 11/08* (2006.01)

(52) U.S. Cl.
USPC ............................. 607/60; 607/32; 128/903

(58) Field of Classification Search
USPC .................. 607/32, 60; 128/903; 340/539.12
See application file for complete search history.

(56) References Cited

U.S. PATENT DOCUMENTS

| | | | |
|---|---|---|---|
| 3,914,586 A | 10/1975 | McIntosh | |
| 4,441,498 A | 4/1984 | Nordling | |
| 4,519,401 A | 5/1985 | Ko et al. | |
| 4,542,535 A | 9/1985 | Bates et al. | |
| 4,543,954 A | 10/1985 | Cook et al. | |
| 4,944,299 A | 7/1990 | Silvian | |
| 4,945,909 A | 8/1990 | Fearnot et al. | |
| 5,230,003 A | 7/1993 | Dent et al. | |
| 5,314,453 A | 5/1994 | Jeutter | |
| 5,342,408 A | 8/1994 | deCoriolis et al. | |
| 5,350,412 A | 9/1994 | Hoegnelid et al. | |
| 5,370,666 A | 12/1994 | Lindberg et al. | |

(Continued)

OTHER PUBLICATIONS

"U.S. Appl. No. 10/870,324, Advisory Action mailed Mar. 21, 2008", 3 pgs.

(Continued)

*Primary Examiner* — Tammie K Heller
(74) *Attorney, Agent, or Firm* — Schwegman Lundberg & Woessner, P.A.

(57) ABSTRACT

An apparatus comprises a transceiver configured to communicate wirelessly with an IMD and a processor communicatively coupled to the transceiver. The processor is configured to detect an error in a data unit received from the IMD, transmit a series of synchronization signals during an uninterrupted communication sequence, and receive, for each synchronization signal, a new data unit and the number of requested duplicate data units from the IMD. Each synchronization signal includes an echo code, wherein the echo code corresponds to a request for a number of duplicate data units to be sent in response to detecting the error in the data unit received during said uninterrupted communication sequence. The number of duplicate data units corresponds to a value of the echo code, and a duplicate data unit corresponds to a data unit previously transmitted by the IMD during said uninterrupted communication sequence.

21 Claims, 4 Drawing Sheets

(56) References Cited

U.S. PATENT DOCUMENTS

| | | | |
|---|---|---|---|
| 5,476,488 A | 12/1995 | Morgan et al. | |
| 5,579,876 A | 12/1996 | Adrian et al. | |
| 5,630,835 A | 5/1997 | Brownlee | |
| 5,650,759 A | 7/1997 | Hittman et al. | |
| 5,683,432 A | 11/1997 | Goedeke et al. | |
| 5,697,958 A | 12/1997 | Paul et al. | |
| 5,745,479 A * | 4/1998 | Burns et al. | 370/245 |
| 5,752,977 A | 5/1998 | Grevious et al. | |
| 5,766,232 A | 6/1998 | Grevious et al. | |
| 5,843,139 A | 12/1998 | Goedeke et al. | |
| 5,861,019 A | 1/1999 | Sun et al. | |
| 5,895,485 A | 4/1999 | Loechel et al. | |
| 5,904,708 A | 5/1999 | Goedeke | |
| 6,009,350 A | 12/1999 | Renken | |
| 6,044,485 A | 3/2000 | Dent et al. | |
| 6,093,146 A | 7/2000 | Filangeri | |
| 6,115,583 A | 9/2000 | Brummer et al. | |
| 6,115,634 A | 9/2000 | Donders et al. | |
| 6,115,636 A | 9/2000 | Ryan | |
| 6,155,208 A | 12/2000 | Schell et al. | |
| 6,169,925 B1 | 1/2001 | Villaseca et al. | |
| 6,275,737 B1 | 8/2001 | Mann | |
| 6,329,920 B1 | 12/2001 | Morrison et al. | |
| 6,336,900 B1 | 1/2002 | Alleckson et al. | |
| 6,385,318 B1 | 5/2002 | Oishi | |
| 6,424,867 B1 | 7/2002 | Snell et al. | |
| 6,427,088 B1 | 7/2002 | Bowman, IV et al. | |
| 6,434,429 B1 | 8/2002 | Kraus et al. | |
| 6,443,891 B1 | 9/2002 | Grevious | |
| 6,456,256 B1 | 9/2002 | Amundson et al. | |
| 6,456,875 B1 | 9/2002 | Wilkinson et al. | |
| 6,470,215 B1 | 10/2002 | Kraus et al. | |
| 6,562,001 B2 | 5/2003 | Lebel et al. | |
| 6,564,104 B2 | 5/2003 | Nelson et al. | |
| 6,564,105 B2 | 5/2003 | Starkweather et al. | |
| 6,574,503 B2 * | 6/2003 | Ferek-Petric | 607/60 |
| 6,574,509 B1 | 6/2003 | Kraus et al. | |
| 6,574,510 B2 | 6/2003 | Von Arx et al. | |
| 6,577,901 B2 | 6/2003 | Thompson et al. | |
| 6,585,644 B2 | 7/2003 | Lebel et al. | |
| 6,600,952 B1 | 7/2003 | Snell et al. | |
| 6,602,191 B2 | 8/2003 | Quy | |
| 6,614,406 B2 | 9/2003 | Amundson et al. | |
| 6,622,043 B1 | 9/2003 | Kraus et al. | |
| 6,622,050 B2 | 9/2003 | Thompson | |
| 6,687,546 B2 | 2/2004 | Lebel et al. | |
| 6,704,602 B2 * | 3/2004 | Berg et al. | 607/60 |
| 6,708,065 B2 | 3/2004 | Von Arx et al. | |
| 7,274,642 B2 | 9/2007 | Sako et al. | |
| 7,457,669 B2 | 11/2008 | Katoozi et al. | |
| 7,519,430 B2 | 4/2009 | Arx et al. | |
| 2001/0027331 A1 | 10/2001 | Thompson | |
| 2001/0047125 A1 | 11/2001 | Quy | |
| 2002/0013614 A1 | 1/2002 | Thompson | |
| 2002/0065539 A1 | 5/2002 | Von Arx et al. | |
| 2002/0147388 A1 | 10/2002 | Mass et al. | |
| 2003/0009203 A1 * | 1/2003 | Lebel et al. | 607/60 |
| 2003/0114898 A1 | 6/2003 | Von Arx et al. | |
| 2004/0030260 A1 | 2/2004 | Von Arx | |
| 2004/0102815 A1 | 5/2004 | Balczewski et al. | |
| 2004/0260363 A1 | 12/2004 | Arx et al. | |
| 2005/0203582 A1 * | 9/2005 | Healy et al. | 607/31 |
| 2005/0283208 A1 | 12/2005 | Von Arx et al. | |
| 2005/0283209 A1 | 12/2005 | Katoozi et al. | |
| 2006/0025834 A1 | 2/2006 | Von Arx et al. | |

OTHER PUBLICATIONS

"U.S. Appl. No. 10/870,324, Examiner Interview Summary mailed Feb. 13, 2008", 4 pgs.

"U.S. Appl. No. 10/870,324, Examiner Interview Summary mailed Sep. 28, 2007", 3 pgs.

"U.S. Appl. No. 10/870,324, Examiner Interview Summary mailed Oct. 25, 2007", 3 pgs.

"U.S. Appl. No. 10/870,324, Final Office Action mailed Jan. 8, 2008", 8 pgs.

"U.S. Appl. No. 10/870,324, Non Final Office Action mailed Jun. 27, 2008", 6 pgs.

"U.S. Appl. No. 10/870,324, Non-Final Office Action mailed May 14, 2008", 8 pgs.

"U.S. Appl. No. 10/870,324, Notice of Allowance mailed Dec. 1, 2008", 7 pgs.

"U.S. Appl. No. 10/870,324, Response filed Feb. 8, 2008 to Final Office Action mailed Jan. 8, 2008", 20 pgs.

"U.S. Appl. No. 10/870,324, Response filed Aug. 14, 2008 to Non-Final Office Action mailed May 14, 2008", 22 pgs.

"U.S. Appl. No. 10/870,324, Response filed Oct. 29, 2007 to Non-Final Office Action mailed Jun. 27, 2007", 21 pgs.

"U.S. Appl. No. 10/870,328, Examiner Interview Summary mailed Apr. 17, 2008", 2 pgs.

"U.S. Appl. No. 10/870,328, Examiner Interview Summary mailed Jul. 24, 2008", 1 pg.

"U.S. Appl. No. 10/870,328, Examiner Interview Summary mailed Nov. 20, 2007", 3 pgs.

"U.S. Appl. No. 10/870,328, Final Office Action mailed Feb. 20, 2008", 10 pgs.

"U.S. Appl. No. 10/870,328, Non Final Office Action mailed Aug. 16, 2007", 12 pgs.

"U.S. Appl. No. 10/870,328, Notice of Allowance mailed Jul. 24, 2008", 10 pgs.

"U.S. Appl. No. 10/870,328, Response filed May 13, 2008 to Final Office Action mailed Feb. 20, 2008", 15 pgs.

"U.S. Appl. No. 10/870,328, Response filed Jun. 8, 2007 to Restriction Requirement mailed Mar. 26, 2007", 12 pgs.

"U.S. Appl. No. 10/870,328, Response filed Nov. 16, 2007 to Non-Final Office Action mailed Aug. 16, 2007", 17 pgs.

"U.S. Appl. No. 10/870,328, Restriction Requirement mailed Mar. 26, 2007", 14 pgs.

Katoozi, M., et al., "On-Demand Retransmission of Data With an Implantable Medical Device", U.S. Appl. No. 10/870,328, filed Jun. 17, 2004, 30 pgs.

Von Arx, J., et al., "Dynamic Telemetry Encoding for an Implantable Medical Device", U.S. Appl. No. 10/870,324, filed Jun. 17, 2004, 39 pgs.

* cited by examiner

ON-DEMAND RETRANSMISSION OF DATA WITH AN IMPLANTABLE MEDICAL DEVICE

CROSS-REFERENCE TO RELATED DOCUMENTS

This application is a Continuation Application of U.S. application Ser. No. 10/870,328, filed on Jun. 17, 2004, now issued as U.S. Pat. No. 7,457,669. This document is related to U.S. patent application Ser. No. 10/870,324, entitled "DYNAMIC TELEMETRY ENCODING FOR AN IMPLANTABLE DEVICE," filed Jun. 17, 2004 by Rawat et al., now issued as U.S. Pat. No. 7,519,430, which is incorporated herein by reference in its entirety.

TECHNICAL FIELD

This document pertains generally to telemetry for medical devices, and more particularly, but not by way of limitation, to on-demand retransmission of data with an implantable medical device.

BACKGROUND

A typical implantable medical device is configured to enable wireless communications with an external device, such as a programmer or a repeater, using inductive telemetry. Inductive telemetry operates using a near field inductive coupling and provides robust communication.

While inductive telemetry tolerates interference from noise sources, many users find that the relatively short communication range is inconvenient.

What is needed is an improved telemetry method and system for robust communication.

BRIEF DESCRIPTION OF THE DRAWINGS

In the drawings, which are not necessarily drawn to scale, like numerals describe substantially similar components throughout the several views. Like numerals having different letter suffixes correspond to different instances of substantially similar components. The drawings illustrate generally, by way of example, but not by way of limitation, various embodiments of the present subject matter.

DETAILED DESCRIPTION

Figure 1:
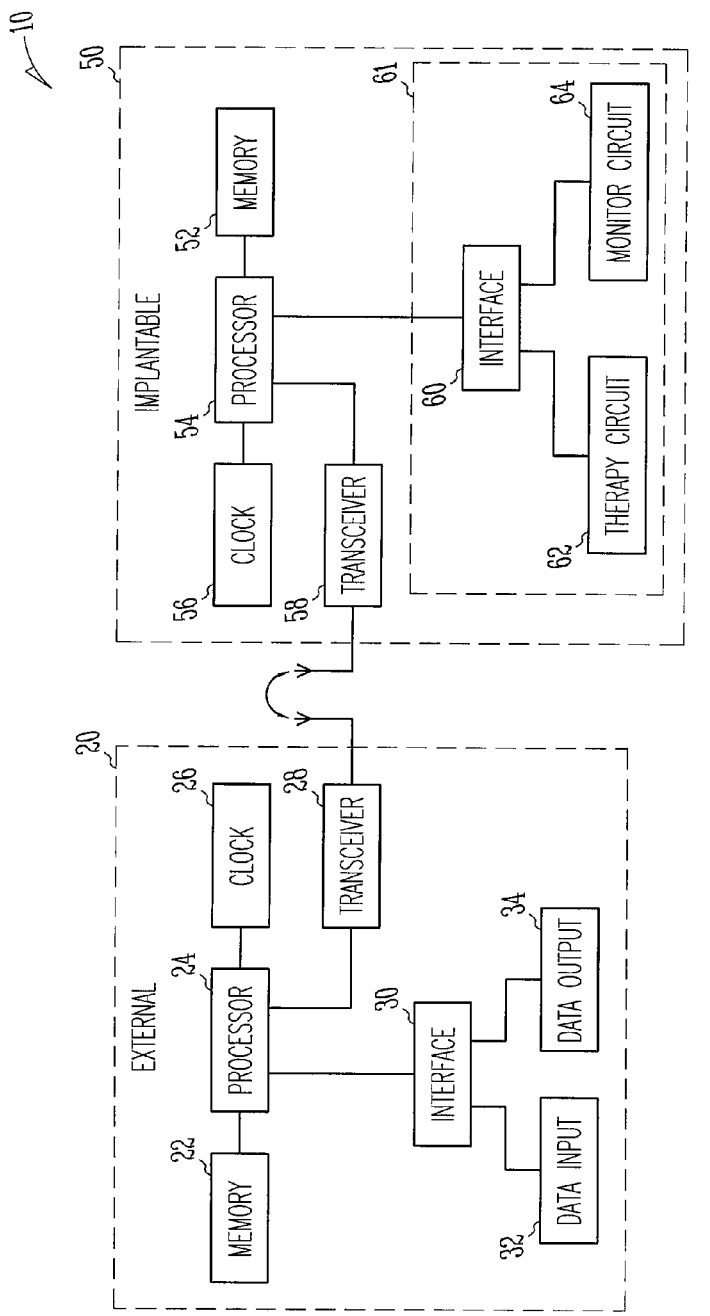
FIG. 1 illustrates an example of a system having an external device and an implantable device configured to communicate wirelessly.

In the following detailed description, reference is made to the accompanying drawings which form a part hereof and which illustrate specific embodiments of the present subject matter. The various embodiments, which are also referred to herein as examples, are described in sufficient detail to enable those skilled in the art to practice the subject matter, and it is to be understood that the embodiments may be combined, or that other embodiments may be utilized and that structural, logical and electrical changes may be made without departing from the scope of the present subject matter. The detailed description is, therefore, not to be taken in a limiting sense and the scope of the present subject matter is defined by the appended claims and their equivalents.

In this document, the articles "a" and "an" denote both the singular and the plural form of the associated noun, and, unless otherwise noted, the term "or" is used in the non-exclusive sense. Furthermore, all publications, patents, and documents referred to in this document are incorporated by reference herein in their entirety, as though individually incorporated by reference. In the event of inconsistencies between this document and those publications, patents and documents herein incorporated by reference, this document is controlling.

System Overview

The present subject matter includes methods and systems for transmitting real time data (such as electrogram data and markers) from an implantable medical device to an external device (such as a programmer or a repeater). The programmer transmits a synchronization signal which, in one example, includes an echo code. The echo code is determined based on data losses caused, for example, by noise or interference in the communication channel. In one example, the echo code is selected based on other criteria.

The implantable device stores a queue of previously transmitted real time data in a memory. As a function of the echo code received with the synchronization signal, the implantable device sends a reply including the real time data appended with selected data from the queue. The programmer, or other external device, utilizes the echoed data in rendering a real time image on a display or in subsequent processing of the data.

The implantable device transmits units of serial data in time-ordered sequence with each unit sent at a time corresponding to a received synchronization signal. The implantable device reads an echo code in the synchronization signal and bundles additional data with each data unit. The additional data is stored in a buffer and selected based on the received echo code. Upon receiving a synchronization signal, the implantable device transmits a reply which includes a data unit along with selected additional data.

The programmer receives, in sequential order, present data units corresponding to a transmitted synchronization signal, and when called for by a transmitted echo code, receives a number of additional data units appended to each present data unit. The additional data units represent redundant data unit derived from earlier data units. The echo code, in various examples, is included with or appended to, the synchronization signal and is used to determine the number of additional data units to be sent with any particular present data unit.

In one example, the implantable device and the external device are configured for telemetry using far field radio frequency communications. Far field communications may be susceptible to drop outs arising from noise and interference sources such as microwave signals and cellular telephones. According to the present subject matter, redundant data is provided by the implantable device upon request, or demand, by the external device. The data is sent in units sometimes referred to as frames or packets.

System

In FIG. 1, system 10 includes external device 20 and implantable device 50 configured for mutual wireless communication.

External device 20 includes processor 24 coupled to memory 22, clock 26, transceiver 28 and interface 30. Interface 30 is further coupled to data input 32 and data output 34. In one example, the combination of data input 32 and interface 30 is referred to as an input interface and is configured to receive, from a user, input data for controlling implantable device 50. In one example, the combination of data output 34 and interface 30 is referred to as an output interface and is configured to provide output information based on a sequence of data units received from implantable device 50.

External device 20, in various examples, include a repeater or a programmer. Processor 24, in various examples, is implemented in circuitry to perform signal processing, a microprocessor configured to execute instructions, or any combination thereof. Processor 24 is configured to implement a method as described elsewhere in this document. Memory 22 provides storage for instructions and data and is sometimes referred to as a storage device. Memory 22 may be included in processor 24 and includes, in various examples, read only memory, random access memory, removable memory and other types of memory. Clock 26 provides timing signals for implementing a method executed by external device 20. Transceiver 28, in one example, includes a far field radio frequency transmitter and a far field radio frequency receiver. Data input 32 receives instructions or data for use by external device 20 or implantable device 50. Data input 32, in various examples, includes memory, a keyboard, a mouse, a trackball, an optical device, an audio transducer or other data input device. Data output 34 renders data derived from external device 20 or implantable device 50. Data output 34, in various examples, includes a printer, a display, a memory and an audio transducer. In one example, data input 32 and data output 34 are combined in a single device. For example, in various examples, data input 32 and data output 34 are instantiated by a touch-sensitive screen or a network interface for coupling to a communication network, such as an Ethernet or other local area network or the internet or other wide area network. Interface 30 serves as an interface between data input 32, data output 34 and processor 24. The foregoing description of external device 20 is not exhaustive and other components or more components are also contemplated. For example, in one example, external device 20 includes multiple processors, one of which is illustrated in the figure and described herein as processor 24. External device 20, in various examples is powered by a metered line service, a battery, or a telephone loop current.

External device 20, according to various examples of the present subject matter, includes a programmer or repeater to facilitate communications with implantable device 50. The programmer, in various examples, includes a display screen, a printer or other output device that conveys data to an operator and receives data or other instructions entered by a human operator or received from an input interface. A repeater, in various examples, includes a device having an interface to a communication network that enables remote monitoring or programming. A repeater, in various examples, refers to a device that communicates between implantable device 50 and a communication network or other device, thereby effectively extending the communication range of implantable device 50. In one example, a repeater is connected to a telephone line within a home thus allowing medical personnel to monitor implantable device 50 of an occupant of the home via the plain old telephone service (POTS) network. In one example, a repeater is communicatively coupled to a network such as the internet by means of a cable modem or other interface. In one example, a repeater include a wireless transceiver for communicating with a long range communication network.

Implantable device 50 includes processor 54 coupled to memory 52, clock 56, transceiver 58 and interface 60. Interface 60 is further coupled to therapy circuit 62 and monitor circuit 64. Implantable device 50, in various examples, includes a cardioverter, a defibrillator, a pacemaker, a therapy device or a monitoring device. Processor 54, in various examples, is implemented in circuitry to perform signal processing, a microprocessor configured to execute instructions, or any combination thereof. In one example, processor 54 includes circuitry or programming to implement an error detection algorithm. Processor 54 is configured to implement a method as described elsewhere in this document. Memory 52 provides storage for instructions or data, sometimes referred to as data units. Memory 52 can be implemented on processor 54 and includes, in various examples, read only memory, random access memory and other types of memory and is sometimes referred to as a storage device. Clock 56 provides timing signals for implementing a method executed by implantable device 50. Transceiver 58, in one example, includes a far field radio frequency transmitter and a far field radio frequency receiver. Therapy circuit 62 delivers therapy to an organ as a function of a signal received from processor 54. Therapy circuit 62, in one example, includes a pulse generator circuit for delivering electrotherapy. Therapy circuit 62, in one example, includes a drug release circuit for delivering a chemical agent as a function of a signal received from processor 54. Monitor circuit 64, in various examples, includes sensors or other devices and circuitry to monitor physiological conditions or events. Monitor circuit 64, in one example, includes sensors and circuitry to monitor parameters and values associated with implantable device 50. For example, in one example, monitor circuit 64 includes a transthoracic impedance measurement circuit. In one example, therapy circuit 62 and monitor circuit 64 are combined in a single device. Interface 60 serves as an interface between therapy circuit 62, monitor circuit 64 and processor 54. In one example, processor 54 is configured to receive a series of data units from data source 61 which includes, for example, interface 60, therapy circuit 62 and monitor circuit 64. Other data sources are also contemplated, including, for example, clock 56, memory 52, processor 54, transceiver 58 or other data sources. The foregoing description of implantable device 50 is not exhaustive and other components or more components are also contemplated. For example, in one example, implantable device 50 includes multiple processors, one of which is illustrated in the figure and described herein as processor 54. Implantable device 50, in various examples, is typically powered by a battery or other energy storage device.

Data Structure and Timing

Figure 2A:
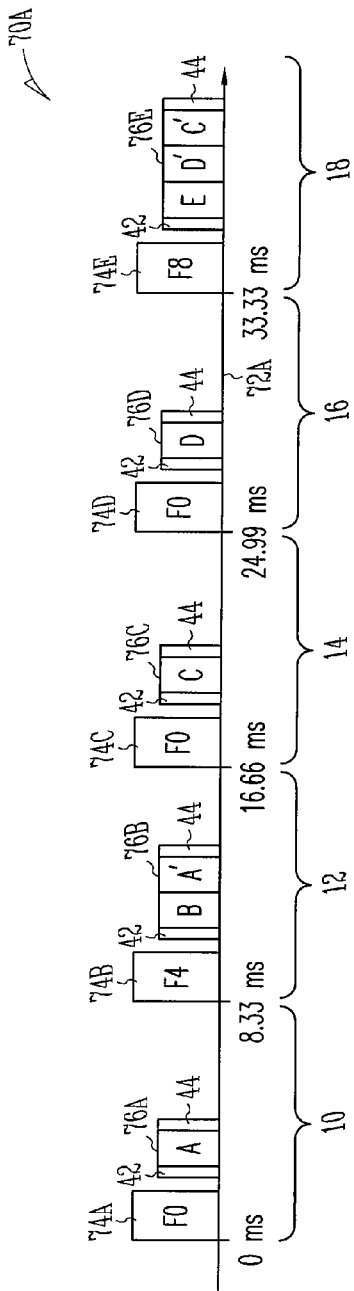
FIGS. 2A and 2B illustrate time lines for an example of a system according to the present subject matter.
Figure 2B:
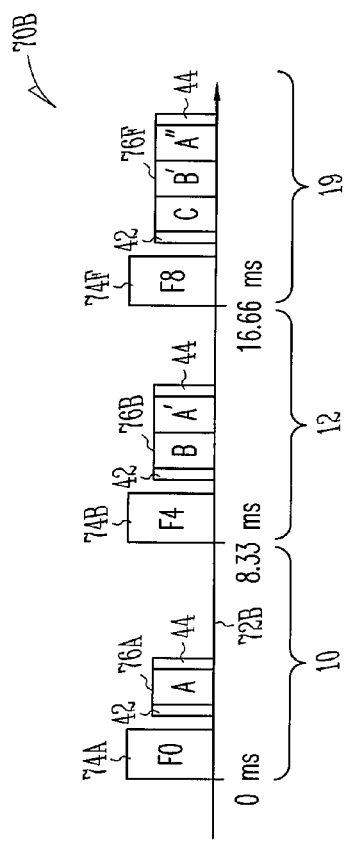

FIGS. 2A and 2B illustrate time lines 70A and 70B, respectively according to one example of the present data communication method. In FIGS. 2A and 2B, the height of the various signals denotes the source of the signal: namely, the taller signals are generated and transmitted by external device 20 and the shorter signals are generated and transmitted by implantable device 50. Axis 72A and axis 72B denote time with those events to the leftward side occurring prior to those events occurring to the rightward side. FIGS. 2A and 2B illustrate data transmitted and received from the perspective of external device 20.

At the outset of time period 10 in FIG. 2A, external device 20 transmits synchronization signal 74A which includes an echo code. In the example illustrated, synchronization signal 74A includes a two bit echo code having a decimal value corresponding to 0, 1 or 2. When expressed in binary characters, the echo code corresponds to the two most significant bits of a half byte, or nibble, having a value of 0000, 0100 or 1000. In one example, the synchronization frame includes other data and the portion referred to as the echo code can have a value, in hexadecimal notation, of F0, F4 and F8. In time period 10, the echo code is denoted as hexadecimal value F0 which corresponds to an echo code value of 0. After a latency period, or turnaround time, during which synchronization signal 74A is propagated, received and processed by implantable device 50, a responsive reply signal 76A is generated by implantable device 50 and transmitted to external device 20. Reply signal 76A includes a real time data unit A in addition to header 42 and footer 44. In one example, footer 44 includes an error detection code. Data unit A, in various examples, typically includes electrogram data or coding event marker data or other data. In the example illustrated, implantable device 50 interprets an echo code of hexadecimal value F0 as corresponding to a request for real time data only.

At the outset of time period 12, external device 20 transmits synchronization signal 74B. In the example illustrated, synchronization signal 74B includes an echo code having a hexadecimal value of F4. After a latency period during which synchronization signal 74B is propagated, received and processed by implantable device 50, a responsive reply signal 76B is generated by implantable device 50 and transmitted to external device 20. Reply signal 76B includes a real time data unit B and data unit A', in addition to header 42 and footer 44. Data unit A' is based on data stored in memory 52 of implantable device 50 and corresponds to real time data unit A which was sent previously in time period 10. In the event that data unit A was corrupted by noise, interference or otherwise includes lost data, then external device 20 selects an echo code value of hexadecimal F4 to trigger implantable device 50 to send an echo, or duplicate of immediately preceding data unit A. The echo of data unit A, as received by external device 20, is denoted here as A' and is referred to as a duplicate data unit or an echo data unit. Data unit B, in various examples, typically includes data from implantable device 50 such as electrogram data or marker data and represents a current data unit or a new data unit. In the example illustrated, implantable device 50 interprets an echo code of value F4 as corresponding to a request for a single unit of echoed data along with a single unit of real time data.

At the outset of time periods 14 and 16, external device 20 transmits synchronization signal 74C and 74D, respectively. In the example illustrated, synchronization signals 74C and 74D each include an echo code having a hexadecimal value of F0. After a latency period during which synchronization signals 74C and 74D are propagated, received and processed by implantable device 50, reply signals are generated and transmitted. Reply signals 76C and 76D, in response to synchronization signals 74C and 74D, respectively, are transmitted by implantable device 50. Reply signals 76C and 74D include real time data units C and D, respectively, in addition to header 42 and footer 44 data. Data units C and D, in various examples, typically includes data from implantable device 50 such as electrogram data or marker data.

At the outset of time period 18, external device 20 transmits synchronization signal 74E. In the example illustrated, synchronization signal 74E includes an echo code having a hexadecimal value of F8. After a latency period during which synchronization signal 74E is propagated, received and processed by implantable device 50, reply signal 76E is generated and transmitted. Reply signal 76E, in response to synchronization signal 74E, is transmitted by implantable device 50. Reply signal 76E includes a real time data unit E and data units D' and C', in addition to header 42 and footer 44 data. Data units D' and C' are based on data stored in memory 52 of implantable device 50 and correspond in value to real time data units D and C, respectively which were sent previously in time periods 14 and 16. In the event that data units C and D were corrupted by noise, interference or otherwise include lost data, then external device 20 selects an echo code hexadecimal value of F8 to trigger implantable device 50 to send an echo of two immediately prior data units, here denoted as C and D. The re-transmitted echoes of data units C and D, as received by external device 20, are denoted here as C' and D'. Data unit E, in various examples, typically includes data from implantable device 50 such as electrogram data or marker data. In the example illustrated, implantable device 50 interprets an echo code of hexadecimal value F8 as corresponding to a request for two units of echoed data along with a single unit of real time data.

Time periods 10 and 12 illustrated in FIG. 2B are the same as those in FIG. 2A. At the outset of time period 19, external device 20 transmits synchronization signal 74F. In the example illustrated, synchronization signal 74F includes an echo code having a hexadecimal value of F8. After a latency period during which synchronization signal 74F is propagated, received and processed by implantable device 50, reply signal 76F is generated and transmitted. Reply signal 76F, in response to synchronization signal 74F, is transmitted by implantable device 50. Reply signal 76F includes a real time data unit C and data units B' and A", in addition to header 42 and footer 44 data. Data unit B' is based on data stored in memory 52 of implantable device 50 and corresponds to real time data unit B which was sent previously in time period 12. Data unit A" is based on data stored in memory 52 of implantable device 50 and corresponds to real time data unit A which was sent initially in time period 10 and an echo of which was sent in time period 12. In the event that data units B and A' were corrupted by noise, interference or otherwise include lost data, then external device 20 selects an echo code value of F8 to trigger implantable device 50 to send an echo of two prior data units, here denoted as B and A'. The echo of data units B and A', as received by external device 20, are denoted here as B' and A". Data unit C, in various examples, includes electrogram data or marker data. In the example illustrated, implantable device 50 interprets an echo code of value F8 as corresponding to a request for two units of echoed data along with a single unit of real time data. In one example, an echo code of value F8 always follows an echo code of value F4.

As illustrated in FIGS. 2A and 2B, each reply from implantable device 50 includes a header 42 and footer 44. Each header 42 and footer 44 may be unique but are illustrated herein with no discernable differences.

In one example, the external device communicates with the implantable device at a communication rate of 120 Hertz. In other words, the external device transmits a synchronization signal, or frame, every 8.333 milliseconds. The rate at which the implantable device samples data is the sampling rate. In one example, electrogram data is generated by sampling the heart at a rate of 400 Hertz. In one example, a communication rate and a sampling rate are selected such that real time data (or new data) and any requested echo data (or duplicate data) can be bundled between successive synchronization signals. Other communication rates and sampling rates are also contemplated.

Figure 3:
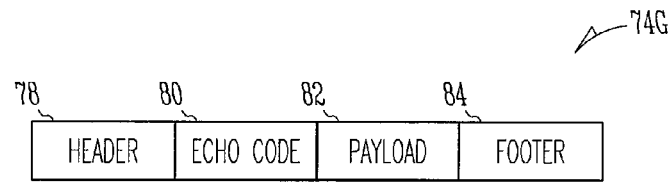
FIG. 3 illustrates an example of a synchronization signal.

FIG. 3 illustrates an example of synchronization signal 74G, sometimes referred to as a synchronization frame. Synchronization signal 74G includes header 78, echo code 80, payload 82 and footer 84. In the example shown in FIG. 3, synchronization signal 74G is a digital signal of 90 bits in length, however other lengths are also contemplated. Header 78, in one example, includes a preamble, an identification code keyed to a specific implantable device and other data. Echo code 80, in one example, includes a two bit value that denotes the amount of requested echo data. These two bits of the echo code are sometimes referred to as command specific bits. In one example, if the first bit in echo code 80 is set in the synchronization frame, then implantable device 50 will interpret this as a request for the previous 5 bytes of electrogram data along with the current, real time, data. In one example, if the second bit in echo code 80 is set, then implantable device 50 will interpret this as a request for the previous 10 bytes of electrogram data along with the current, real time, data. In one example, the second bit of echo code 80 has priority and if set, then the first bit of echo code 80 is ignored and the 10 previous bytes will be sent. Payload 82, in one example, includes a payload having a variable value. Footer 84, in one example, includes an error detection code.

In one example, an error detection code is included in the synchronization frame sent by external device 20. In one example, an error detection code is included in the reply signal sent by implantable device 50. In various examples, the error detection code includes a cyclic redundancy check code or a checksum. According to one example, the sending device calculates a cyclic redundancy check code for the data to be transmitted and appends that code to the packet or frame. The receiving device calculates a new cyclic redundancy check code, using the same algorithm, based on the received packet or frame. An error is detected when a difference exists between the code received with the packet and the calculated code.

If, in the example above, the programmer is the receiving device and an error is detected, then the programmer sends an echo code in the next synchronization frame. The echo code indicates to the implantable device that an error was detected and also provides instructions for the implantable device as to what further action is to be taken.

In one example, the synchronization frame transmitted by external device 20 has a length of 90 bits and the header and footer in the reply signal transmitted by implantable device 50 are of length 70 bits and 20 bits, respectively. In one example, each unit of electrogram or other data includes 50 bits.

Method

Figure 4:
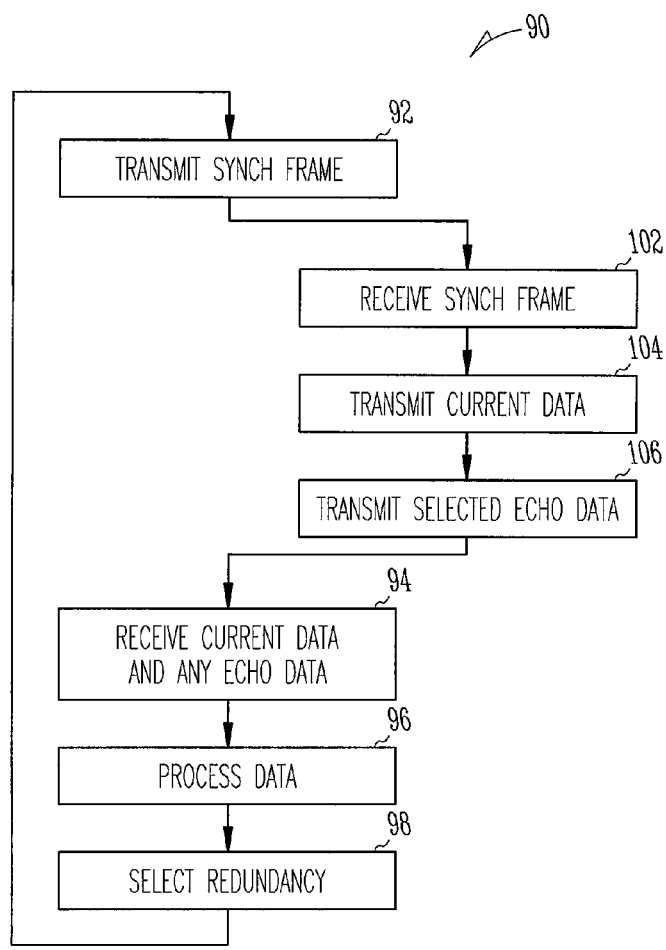
FIG. 4 illustrates a flow chart of a method pursuant to one example of the present subject matter.

FIG. 4 illustrates a flow chart of one example of method 90. In the figure, external device 20 transmits a synchronization frame at 92. In one example, the synchronization frame includes an echo code, or flag, used to enable a level of redundancy. In one example, the echo code is appended to the synchronization frame. At 102, implantable device 50 then receives the synchronization frame. Following a latency period, implantable device 50 responds at 104 by transmitting new, or current, data. The new data, in various examples, corresponds to physiological data, electrogram data, marker data or other measured real time or stored data. In one example, the new data is generated by a data source such as, for example, a physiological sensor circuit, a monitor circuit, a pulse generator or an intercardiac electrogram and buffered or stored in a memory. Implantable device 50 decodes the echo code and accesses memory 52 as a function of the echo code to obtain echo or duplicate data units. For example, in one example, processor 54 selectively access data units stored in memory 52. If directed by the echo code, at 106, implantable device 50 transmits the selected echo data units retrieved from memory 52. In one example, memory 52 is configured to store at least three data units representing three echo data units or two echo data units and one current data unit.

At 94, external device 20 then receives the current data unit along with any echo data units as specified by the echo code. At 96, external device 20 processes the received data. In various examples, this includes detecting errors using an error detection code, replacing previously received and erroneous data with replacement data, generating real time images for display, storing data or other processing functions. In one example, an image is rendered on a display of external device 20 as a function of a present data unit and one or more echo data units. At 98, the method continues with external device 20 executing an algorithm to select a level of redundancy for a subsequent synchronization frame. In one example, selecting a level of redundancy, and thus a value for the echo code, includes determining an error status for previously received data. In one example, the level of redundancy is selected by a flag or other code stored in memory and is valid for a specified duration or a particular communication session. In one example, the echo code is remotely selectable by a user or by other criteria. Following 98, processing continues with external device 20 transmitting a subsequent synchronization frame. In one example, method 90 is repeatedly executed during a communication session. In one example, implantable device 50 receives a sequence of synchronization signals transmitted from external device 20 and a sequence of data units is transmitted from implantable device 50 for reception by external device 20. Each data unit, along with any corresponding echo data unit, is in one to one relation with a synchronization signal. According to one example, external device 20 executes portions of method 90 denoted here as 92, 94, 96 and 98 and implantable device 50 executes portions of method 90 denoted here as 102, 104 and 106.

Synchronization Signal Detection

As noted, the present subject matter can be configured to correct errors noted in data transmitted from the implantable device and received by the external device. In addition, the present subject matter can be configured to correct errors in data transmitted from the external device and received by the implantable device.

Figure 5:
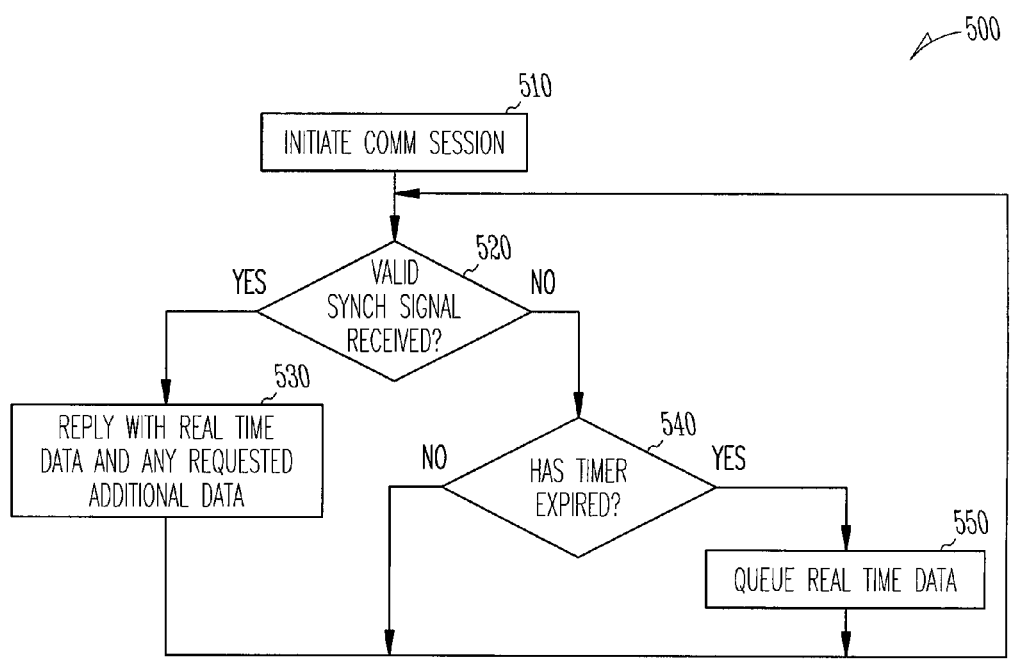
FIG. 5 illustrates a flow chart of a method performed by an implantable device pursuant to one example of the present subject matter.

FIG. 5 illustrates method 500 in which the implantable device detects an error in data transmitted by the external device. For example, if the synchronization signal is corrupted with noise, the implantable device preserves the sampled data in sequential order and awaits receipt of a clean synchronization signal. Method 500 can be implemented in software, firmware, hardware or any combination thereof.

At 510, the communication session is initiated using either a near field or a far field telemetry link. At 520, a query is presented to determine if a valid synchronization signal has been received. If the outcome of the query is affirmative, then at 530, the implantable device generates and transmits a reply including real time data along with any requested additional data stored in a memory or queue of implantable device 50. A negative outcome of the query would indicate that the synchronization signal was sufficiently noisy, missing or otherwise unintelligible. At 540, implantable device 50 determines if a timer for the synchronization signal has expired. If the timer for the synchronization signal has elapsed, then, at 550, sampled data is queued in a memory of device 50 after which method 500 returns to the query at 520. If, on the other hand, the timer has not expired, then the method continues by listening for a synchronization signal. The sampled data includes real time data and is queued up in a memory that preserves the time order of the data. In one example, the real time data, or current data unit, is stored in a queue with each queue entry corresponding to an estimated time of occurrence of the synchronization signal. In other words, the estimated time of occurrence of the synchronization signal is correlated, or associated with, the stored current data unit.

In one example, clock 56 provides a timing signal which is used to estimate the occurrence of a corrupted or missing synchronization signal. An error detector of implantable device 50 is used to determine if a received signal includes a synchronization signal and to identify an error in an inbound signal received from the external device. The error detector can be implemented in any combination of software, firmware or hardware and in various examples, includes a comparator or a processor executing a comparison algorithm.

In one example, the implantable device includes a storage device, a processor and a transceiver. The transceiver receives an inbound signal and determines if the inbound signal includes a synchronization signal. If the inbound signal includes a synchronization signal, then the processor selects and transmits outbound data from a queue of data stored in the storage device. The outbound data is selected based on an echo code in the synchronization signal.

In one example, the implantable device monitors for an inbound signal and determines if the inbound signal includes a synchronization signal. If the inbound signal includes a synchronization signal, then a reply signal is transmitted from the implantable device. The reply signal includes a current data unit and a number of duplicate data units, where the number of duplicate data units is selected as a function of an echo code of the synchronization signal. If the inbound signal does not include a synchronization signal, then the implantable device generates an estimate of a time of occurrence of the synchronization signal and stores the current data unit in a queue in a storage device.

ALTERNATIVE EXAMPLES

The present subject matter is described relative to wireless communications using far field radio frequency transmission and reception. However, the disclosed subject matter is also suitable for use with near field transmission and reception, such as that provided by an inductive coupling.

In one example, the echo code in the synchronization frame is selected as a function of an error code calculated based on a previously received reply signal. In various examples, the echo code is set to a value based on other criteria. According to one example, when communicating in an environment known to be noisy, the programmer is configured to set the echo code for a particular communication session to request a predetermined level of redundant or echo data. In one example, the programmer, or other external device, is configured to select an echo code based on user input, time of day, location, measured parameter or other criteria.

In one example, the implantable device is powered by a battery and redundant data is requested on an as-needed basis. Consequently, the power consumption of the transmitter of the implantable device is less than that associated with continuously transmitting redundant data.

In one example, the external device functions as the master and the implantable device is the slave. As such the external device generates and transmits the synchronization signal and the implantable device responds by synchronizing with the received signal and transmitting the data requested in the synchronization signal.

In one example, the implantable device is configured to listen to the communication channel during predetermined periods of time. If the implantable device detects a synchronization signal, or any portion thereof, then the implantable device enters a mode in which the reply signals are generated and transmitted as described elsewhere in this document. For example, in one example, the implantable device periodically monitors the communication channel for a preamble which includes a code that identifies the particular implantable device.

In one example, the echo code has a length of 2 bits which can specify 4 discrete modes for redundancy. Echo codes of lengths greater or less than 2 bits are also contemplated, in which case more or less than 4 modes are selectable.

In one example, the storage capacity of memory 52 of implantable device 50 is configured to accommodate the desired number of redundant data units. Memory 52 operates as a running buffer which stores a number of most recent data units and discards older data units.

In one example, multiple channels of data are transmitted using the subject matter described herein. For example, in one example, the reply signal includes two bytes of atrial data, two bytes of ventricular data and one byte of marker data. Other heart data is also contemplated for the reply signal.

In one example, the data is transmitted in serial manner and arranged such that the current real time data unit precedes any echo data unit. Other configurations are also contemplated, including for example, a serial transmission where the echo data units are appended to the current data unit.

Error detection codes other than a cyclic redundancy check code and a checksum are also contemplated. For example, in one example, the error detection code includes a parity check.

In one example, implantable device 50 includes an error detection code calculator coupled to transceiver 58 and configured to determine an error detection code as a function of a present data unit and a number of echo data units as determined by a received echo code. The error detection code calculator, in various examples, is implemented in an executable algorithm, an electrical circuit or any combination of an algorithm and a circuit. In one example, external device 20 includes a comparator coupled to transceiver 28 and is configured to generate an output based on a comparison of the error code and a code calculated by a code generator. The code generator is configured to detect an error code based on the received data. In one example, the echo code is generated as a function of the output from the comparator. In one example, the comparator and the code generator are implemented in an algorithm executed by processor 24.

In one example, the external device requests duplicate or echo data units from the implantable device. In one example, the implantable device requests duplicate or echo data units from the external device using the methods and devices described herein.

It is to be understood that the above description is intended to be illustrative, and not restrictive. For example, the above-described examples, or any portion thereof, may be used in combination with each other. In the appended claims, the phrase "any combination" includes a single element as well as multiple elements. Furthermore, the transitional terms comprising and including are used in the open ended sense in that elements in addition to those enumerated may also be present. Other examples will be apparent to those of skill in the art upon reviewing this document.

What is claimed is:

1. A method comprising:
   transmitting, using an external device, a series of synchronization signals during an uninterrupted communication mode, wherein each synchronization signal includes an echo code, wherein the transmitted echo code requests a number of duplicate data units to be sent in response to detecting an error in a data unit received by the external device during said uninterrupted communication mode; and
   receiving, using the external device and for each synchronization signal, a new data unit and receiving the number of requested duplicate data units from an implantable medical device (IMD), wherein the number is selected using a value of the echo code, and wherein a duplicate data unit corresponds to a data unit previously transmitted by the IMD during said uninterrupted communication mode.

2. The method of claim 1, wherein transmitting includes transmitting a far field radio frequency signal.

3. The method of claim 1, further including rendering an image on a display using a received new data unit and any received duplicate data units.

4. The method of claim 1, wherein each duplicate data unit corresponds to a previously transmitted new data unit.

5. The method of claim 1, wherein the echo code includes a two bit value.

6. The method of claim 1, wherein the number is selected from the group of 0, 1and 2.

7. The method of claim 1, wherein receiving the new data unit and receiving the number of duplicate data units includes receiving the new data unit before receiving the number of duplicate data units.

8. The method of claim 1, further including generating an error code based on the received new data unit and the number of duplicate data units.

9. The method of claim 8, wherein the echo code is selected as a function of the error code.

10. The method of claim 9, wherein the echo code corresponds to a request for greater than zero duplicate data units.

11. The method of claim 1, wherein the echo code is remotely selectable.

12. The method of claim 1, wherein a data unit may be transmitted multiple times as a duplicate data unit during the same communication sequence.

13. The method of claim 1, wherein at least one unit of real time data from the implantable device is received by the external device for a synchronization signal transmitted by the external device during the uninterrupted communication mode.

14. An apparatus comprising:
a transceiver configured to communicate wirelessly with an IMD;
a processor communicatively coupled to the transceiver, wherein the processor is configured to:
detect an error in a data unit received from the IMD;
transmit via the transceiver, during an uninterrupted communication mode, a series of synchronization signals wherein each synchronization signal includes an echo code, wherein the transmitted echo code requests a number of duplicate data units to be sent in response to detecting the error in the data unit received via the transceiver during said uninterrupted communication mode; and
receive via the transceiver, for each synchronization signal, a new data unit and the number of requested duplicate data units from the IMD, wherein the number of duplicate data units corresponds to a value of the echo code, and wherein a duplicate data unit corresponds to a data unit previously transmitted by the IMD during said uninterrupted communication mode.

15. The apparatus of claim 14, wherein the processor is configured to request that a data unit is transmitted multiple times as a duplicate data unit during the same communication sequence.

16. The apparatus of claim 14, including a display communicatively coupled to the processor, and wherein the processor is configured to render an image on the display using a received new data unit and any received duplicate data units.

17. The apparatus of claim 16, wherein the processor is configured to display at least one of electrogram data and marker data using the duplicate data units.

18. The apparatus of claim 17, wherein a data unit includes multiple bytes of at least one of electrogram data and marker data.

19. The apparatus of claim 14, wherein the processor is configured to generate an error code based on the received new data unit and the number of duplicate data units.

20. The apparatus of claim 19, wherein the processor is configured to generate the echo code based on the generated error code.

21. The apparatus of claim 14, wherein the processor is configured to generate the echo code according to a requested data redundancy level entered by a user.

* * * * *